US012558570B2

(12) United States Patent
Suthanthiran et al.

(10) Patent No.: US 12,558,570 B2
(45) Date of Patent: Feb. 24, 2026

(54) 70 MEV TO 150 MEV CYCLOTRON DEDICATED FOR MEDICAL TREATMENT INCLUDING A ROBOTIC CHAIR/TABLE

(71) Applicant: Best Theratronics Ltd., Kanata (CA)

(72) Inventors: Krishnan Suthanthiran, Lorton, VA (US); Manny Subramanian, Frederick, MD (US); Toby Henderson, Rockford, IL (US); Vasile Sabaiduc, Richmond (CA); Richard Johnson, Vancouver (CA); Leandro Piazza, Vancouver (CA); Vladimir Ryjkov, Burnaby (CA)

(73) Assignee: Best Theratronics, Ltd. (CA)

( * ) Notice: Subject to any disclaimer, the term of this patent is extended or adjusted under 35 U.S.C. 154(b) by 546 days.

(21) Appl. No.: 17/995,630

(22) PCT Filed: Apr. 7, 2021

(86) PCT No.: PCT/CA2021/050460
§ 371 (c)(1),
(2) Date: Oct. 6, 2022

(87) PCT Pub. No.: WO2021/203196
PCT Pub. Date: Oct. 14, 2021

(65) Prior Publication Data
US 2023/0256267 A1 Aug. 17, 2023

Related U.S. Application Data

(60) Provisional application No. 63/007,303, filed on Apr. 8, 2020.

(51) Int. Cl.
*A61N 5/10* (2006.01)
*H05H 13/00* (2006.01)

(52) U.S. Cl.
CPC ........... *A61N 5/107* (2013.01); *A61N 5/1049* (2013.01); *A61N 5/1067* (2013.01);
(Continued)

(58) Field of Classification Search
CPC .... A61N 5/107; A61N 5/1049; A61N 5/1067; A61N 5/1068; A61N 5/1078;
(Continued)

(56) References Cited

U.S. PATENT DOCUMENTS

| | | |
|---|---|---|
| 3,981,769 A | 9/1976 | Winchell |
| 4,112,306 A | 9/1978 | Nunan |
| | (Continued) | |

FOREIGN PATENT DOCUMENTS

| | | |
|---|---|---|
| EP | 2372720 A1 | 10/2011 |
| WO | 2013084004 A1 | 6/2013 |
| | (Continued) | |

OTHER PUBLICATIONS

International Search Report and Written Opinion of the International Searching Authority dated Jun. 10, 2021; International Application No. PCT/CA2021/050460; Canadian Intellectual Property Office; Gatineau, Quebec, Canada.
(Continued)

*Primary Examiner* — David A Vanore
(74) *Attorney, Agent, or Firm* — Stevens & Showalter LLP

(57) ABSTRACT

A proton cyclotron is provided for dedicated use in head, neck and eye cancers, tumors or other medical conditions including pediatric and other cancers or medical conditions. The method of using a proton cyclotron for treating a tumor, cancer or medical condition of a patient includes positioning the patient on a support platform, such as on a patient table or in a robotic chair, and irradiating the tumor, cancer or other medical condition using a proton particle beam from (Continued)

the cyclotron for a predetermined time sufficient to treat the tumor, cancer or medical condition, wherein the proton particle beam produced by the cyclotron has an energy in a range of 70 MeV to 150 MeV and has a beam current in an amount suitable for radiation therapy, as can include a variable range of beam current for the radiation therapy.

16 Claims, 3 Drawing Sheets

(52) U.S. Cl.
CPC ......... *A61N 5/1068* (2013.01); *A61N 5/1078* (2013.01); *H05H 13/005* (2013.01); *A61N 2005/1061* (2013.01); *A61N 2005/1087* (2013.01); *A61N 2005/1097* (2013.01); *H05H 2277/11* (2013.01)

(58) Field of Classification Search
CPC .... A61N 2005/1061; A61N 2005/1087; A61N 2005/1097; H05H 13/005; H05H 2277/11
See application file for complete search history.

(56) References Cited

U.S. PATENT DOCUMENTS

| | | | |
|---|---|---|---|
| 4,139,777 A | | 2/1979 | Rautenbach |
| 4,507,616 A | * | 3/1985 | Blosser .................... A61N 5/10 376/112 |
| 4,641,104 A | * | 2/1987 | Blosser .................... H05H 7/20 376/112 |
| 4,870,287 A | * | 9/1989 | Cole ........................ G21K 5/10 250/398 |
| 5,139,731 A | | 8/1992 | Hendry |
| 5,479,023 A | | 12/1995 | Bartle |
| 5,547,454 A | * | 8/1996 | Horn .................... A61N 5/1077 600/1 |
| 7,554,275 B2 | | 6/2009 | Amaldi |
| 7,888,891 B2 | | 2/2011 | Iida et al. |
| 8,229,072 B2 | * | 7/2012 | Balakin .................... A61N 5/10 378/65 |
| 8,399,866 B2 | * | 3/2013 | Balakin .................... H05H 7/10 315/504 |
| 8,519,365 B2 | * | 8/2013 | Balakin ................ A61N 5/1064 250/492.3 |
| 8,659,243 B2 | | 2/2014 | Morita et al. |
| 8,779,939 B2 | | 7/2014 | Barth et al. |
| 9,056,199 B2 | * | 6/2015 | Balakin .................. H05H 13/04 |
| 9,274,067 B2 | * | 3/2016 | Schulte .................. A61B 6/548 |
| 9,597,243 B1 | * | 3/2017 | Helmick ................ A61G 15/12 |
| 9,682,254 B2 | * | 6/2017 | Balakin ................ A61N 5/1081 |
| 9,737,731 B2 | * | 8/2017 | Balakin ................ G21K 1/093 |
| 9,950,194 B2 | * | 4/2018 | Bouchet .............. A61N 5/1049 |
| 10,183,179 B1 | * | 1/2019 | Smith .................. A61N 5/1069 |
| 10,363,439 B2 | * | 7/2019 | Amaldi ................ H05H 9/041 |
| 11,426,603 B2 | * | 8/2022 | Kobashi .............. A61N 5/1037 |
| 11,648,420 B2 | * | 5/2023 | Balakin ................ A61N 5/1082 600/427 |
| 2002/0099405 A1 | | 7/2002 | Yurek et al. |
| 2004/0162457 A1 | * | 8/2004 | Maggiore ............ A61N 5/1079 600/1 |
| 2006/0002511 A1 | * | 1/2006 | Miller .................... A61N 5/107 378/65 |
| 2007/0169265 A1 | * | 7/2007 | Saracen .............. A61B 6/0487 5/601 |
| 2007/0189461 A1 | * | 8/2007 | Sommer .............. A61N 5/1049 378/178 |
| 2008/0191142 A1 | * | 8/2008 | Pedroni .............. A61N 5/1049 250/396 ML |
| 2009/0003532 A1 | * | 1/2009 | Weber .................. A61B 6/0487 378/209 |
| 2009/0209805 A1 | | 8/2009 | Lubock et al. |
| 2009/0309038 A1 | * | 12/2009 | Balakin .................... H05H 7/10 250/492.3 |
| 2009/0309040 A1 | * | 12/2009 | Balakin ................. H05H 13/04 250/492.3 |
| 2009/0309046 A1 | * | 12/2009 | Balakin .................. H05H 13/04 378/65 |
| 2009/0314960 A1 | * | 12/2009 | Balakin ................. A61N 5/1049 250/492.3 |
| 2009/0314961 A1 | * | 12/2009 | Balakin ................. G21K 1/093 250/492.3 |
| 2010/0006770 A1 | * | 1/2010 | Balakin .................... H01J 3/14 378/65 |
| 2010/0008466 A1 | * | 1/2010 | Balakin ................. H05H 13/04 378/65 |
| 2010/0027745 A1 | * | 2/2010 | Balakin .............. A61B 6/4092 378/65 |
| 2010/0046697 A1 | * | 2/2010 | Balakin ................. H05H 13/04 250/306 |
| 2010/0059687 A1 | * | 3/2010 | Balakin ................. H05H 13/04 250/492.3 |
| 2010/0060209 A1 | * | 3/2010 | Balakin .................... H05H 7/10 315/505 |
| 2010/0127184 A1 | * | 5/2010 | Balakin ................ A61N 5/1049 250/492.3 |
| 2010/0133444 A1 | * | 6/2010 | Balakin ................. H05H 13/04 250/491.1 |
| 2010/0133446 A1 | * | 6/2010 | Balakin ................. H05H 13/04 250/397 |
| 2010/0171447 A1 | * | 7/2010 | Balakin ................. H05H 13/04 315/503 |
| 2010/0207552 A1 | * | 8/2010 | Balakin .................... H05H 7/10 315/503 |
| 2010/0215137 A1 | | 8/2010 | Nagai et al. |
| 2010/0266100 A1 | * | 10/2010 | Balakin .................... A61N 5/10 378/65 |
| 2011/0150180 A1 | * | 6/2011 | Balakin .................... H05H 7/04 378/65 |
| 2011/0180720 A1 | * | 7/2011 | Balakin .................. G21K 1/087 250/396 ML |
| 2011/0180731 A1 | * | 7/2011 | Welsh .................... A61N 5/103 378/65 |
| 2011/0182410 A1 | * | 7/2011 | Balakin ................. G21K 1/087 378/65 |
| 2011/0218430 A1 | * | 9/2011 | Balakin .................... H05H 7/04 250/453.11 |
| 2011/0313232 A1 | * | 12/2011 | Balakin ................ A61N 5/1081 315/503 |
| 2012/0190171 A1 | | 7/2012 | Yamazaki et al. |
| 2013/0105702 A1 | * | 5/2013 | Balakin ................. H05H 13/04 250/396 ML |
| 2015/0217140 A1 | * | 8/2015 | Balakin .................. A61N 5/107 600/1 |
| 2016/0250501 A1 | * | 9/2016 | Balakin ................. A61B 6/025 600/1 |
| 2016/0279443 A1 | * | 9/2016 | Bennett ................ A61N 5/1067 |
| 2016/0317838 A1 | * | 11/2016 | Michaud ............. A61N 5/1082 |
| 2016/0354048 A1 | * | 12/2016 | Lee ...................... G21K 5/04 |
| 2016/0354616 A1 | * | 12/2016 | Lee ...................... G01N 23/046 |
| 2016/0367207 A1 | * | 12/2016 | Michaud ............. A61B 6/0487 |
| 2016/0375269 A1 | * | 12/2016 | Michaud ............... A61B 6/032 600/1 |
| 2017/0014646 A1 | * | 1/2017 | Lee ...................... A61N 5/1067 |
| 2017/0014647 A1 | * | 1/2017 | Michaud ............. A61B 6/4258 |
| 2017/0036041 A1 | * | 2/2017 | Reichert .............. A61B 6/032 |
| 2017/0043187 A1 | * | 2/2017 | Lee ...................... A61N 5/1044 |
| 2017/0056688 A1 | * | 3/2017 | Penfold .............. A61N 5/1049 |
| 2017/0113067 A1 | * | 4/2017 | Lee ...................... A61N 5/1037 |
| 2017/0128029 A1 | * | 5/2017 | Penfold .............. A61B 6/4258 |
| 2017/0128747 A1 | * | 5/2017 | Bennett .................. G21K 1/08 |
| 2017/0150934 A1 | * | 6/2017 | Bennett ................ A61N 5/1077 |
| 2017/0189722 A1 | * | 7/2017 | Reno ...................... G21K 1/08 |
| 2017/0197097 A1 | * | 7/2017 | Michaud ............. A61N 5/1069 |
| 2017/0197099 A1 | * | 7/2017 | Ruebel ................ A61N 5/1049 |
| 2017/0203124 A1 | * | 7/2017 | Reno ...................... A61N 5/1037 |
| 2017/0203125 A1 | * | 7/2017 | Amato ................ A61N 5/1039 |
| 2017/0209714 A1 | * | 7/2017 | Bennett ................ A61N 5/1037 |
| 2017/0348547 A1 | * | 12/2017 | Lee ...................... A61N 5/1037 |

(56) References Cited

U.S. PATENT DOCUMENTS

| | | | | |
|---|---|---|---|---|
| 2018/0012727 | A1* | 1/2018 | Amato | A61B 6/4035 |
| 2018/0078790 | A1* | 3/2018 | Lee | G21K 5/10 |
| 2018/0099156 | A1* | 4/2018 | Elgart | A61N 5/1049 |
| 2018/0161601 | A1* | 6/2018 | Spotts | G21K 5/04 |
| 2018/0169440 | A1 | 6/2018 | Liu et al. | |
| 2018/0169441 | A1* | 6/2018 | Spotts | G21K 5/10 |
| 2018/0178039 | A1* | 6/2018 | Petterson | A61B 6/032 |
| 2018/0178040 | A1* | 6/2018 | Penfold | G21K 5/04 |
| 2018/0185673 | A1* | 7/2018 | Lee | G21K 1/093 |
| 2018/0200539 | A1* | 7/2018 | Amato | A61N 5/1082 |
| 2018/0250528 | A1 | 9/2018 | Liu et al. | |
| 2018/0326225 | A1 | 11/2018 | Liu et al. | |
| 2019/0021684 | A1* | 1/2019 | Ruebel | A61N 5/1082 |
| 2019/0111284 | A1* | 4/2019 | Lee | G21K 5/10 |
| 2019/0175947 | A1* | 6/2019 | Patch | A61N 5/1067 |
| 2019/0351258 | A1* | 11/2019 | Elgart | A61B 6/03 |
| 2019/0358471 | A1* | 11/2019 | Raymond | A61B 6/4092 |
| 2019/0366125 | A1* | 12/2019 | Petterson | A61B 6/03 |
| 2020/0227227 | A1* | 7/2020 | Balakin | A61N 5/1043 |
| 2020/0269068 | A1* | 8/2020 | Abel | A61N 5/1077 |
| 2020/0406063 | A1* | 12/2020 | Petterson | A61B 6/4092 |
| 2021/0178193 | A1* | 6/2021 | Spotts | A61N 5/1044 |
| 2021/0274634 | A1* | 9/2021 | Amaldi | H05H 9/041 |
| 2021/0275833 | A1* | 9/2021 | Krishnaswamy | A61B 5/0077 |
| 2021/0322788 | A1* | 10/2021 | Liu | A61N 5/1031 |
| 2021/0353966 | A1* | 11/2021 | Michaud | A61N 5/1044 |
| 2021/0370101 | A1* | 12/2021 | Michaud | A61N 5/1067 |
| 2021/0387022 | A1* | 12/2021 | Raymond | G21K 1/10 |
| 2021/0393987 | A1* | 12/2021 | Michaud | A61N 5/1044 |
| 2021/0393988 | A1* | 12/2021 | Raymond | A61N 5/1081 |
| 2022/0044835 | A1* | 2/2022 | Guerin | A61K 51/083 |
| 2022/0249872 | A1* | 8/2022 | Seco | A61N 5/1071 |
| 2022/0296926 | A1* | 9/2022 | Kolesnick | A61N 5/1031 |
| 2023/0204528 | A1 | 6/2023 | Johnson et al. | |
| 2023/0209697 | A1 | 6/2023 | Johnson et al. | |

FOREIGN PATENT DOCUMENTS

| | | | |
|---|---|---|---|
| WO | 20210217249 | A1 | 11/2021 |
| WO | 20210217258 | A1 | 11/2021 |

OTHER PUBLICATIONS

Keizo Ishii; "Pixe and Its Applications to Elemental Analysis"; Quantum Beam Science; 3, 12; MDPI; Jun. 10, 2019; https://doi.org/10.3390/qubs3020012.

Milos Budnar et al.; "In-Air PIXE Set-Up for Automatic Analysis of Historical Document Inks"; Nuclear Instruments and Methods in Physics Research Section B: Beam Interactions with Materials and Atoms, vols. 219-220, Jun. 2004, Elsevier Science Direct; pp. 41-47; https://doi.org/10.1016/j.nimb.2004.01.025.

G. Demortier and F. Bodart; "Complementarity of PIXE and PIGE for the Characterization of Gold Items of Ancient Jewelry"; J. Radioanal. Chem. 69; Springer Nature; Mar. 1982; https://doi.org/10.1007/BF02515927.

T. Mitsumoto et al. "Cyclotron-Based Neutron Source for BNCT"; AIP Conference Proceedings 1525; AIP Publishing; Apr. 2013; https://doi.org/10.1063/1.4802341.

C.M. York et al.; "Neutron Beam From the UCLA Spiral-Ridge Cyclotron"; Proceedings of the International Conference on Sector-Focused Cyclotrons and Meson Factories; Geneva, Apr. 23-26, 1963.

K. Erdman et al.; "Compact Commercial 9 MeV Deuteron Cyclotron with Pulsed Beam"; Cyclotrons and Their Applications 2001, Sixteenth International Conference, American Institute of Physics; AIP Publishing; 2001.

W.A. Lanford et al.; "Nuclear Reaction Analysis for H,Li, Be, B, C, N, O and F with an RBS Check"; Nuclear Instruments and Methods in Physics Research Section B; Beam Interactions with Materials and Atoms; Elsevier Publishing; Nov. 2015.

G.W. Grime et al.; "Nuclear Microscopy of Inhomogeneous Thick Samples"; Nuclear Instruments and Methods in Physics Research B54; Elsevier Science Publishers B.V.; North-Holland; 1991.

Hassan Bayaa; International Search Report and Written Opinion; Application No. PCT/CA2021/050583; Jul. 22, 2021; CIPO; Quebec, Canada.

Omer Ondun; International Search Report and Written Opinion; Application No. PCT/CA2021/050567; Jul. 22, 2021; CIPO; Quebec, Canada.

Tsai, Hsien C; Non-Final Rejection dated Jun. 9, 2025; U.S. Appl. No. 17/922,468; United States Patent and Trademark Office; Alexandria, Virginia.

* cited by examiner

70 MEV TO 150 MEV CYCLOTRON DEDICATED FOR MEDICAL TREATMENT INCLUDING A ROBOTIC CHAIR/TABLE

FIELD OF THE INVENTION

The present invention relates generally to cyclotrons and particularly to a hydrogen (proton) cyclotron for dedicated use in treating various medical conditions, including but not limited to benign and malignant tumors, neurological, lung, head, neck and eye tumors, cancers, abnormalities or conditions, vascular and cardiac conditions and abnormalities, pediatric tumors and other pediatric abnormalities, and other medical conditions, suitable for treatment with radiation therapy.

BACKGROUND

Cyclotrons have been known for many years. A cyclotron is one type of particle accelerators in which charged particles are accelerated through a substantially spiral path using the forces of electrical potential and magnetic fields. The first cyclotron was invented by Ernest O. Lawrence in 1929-1930 at the University of California, Berkeley, for which he was awarded the Nobel Prize in Physics in 1939.

A cyclotron accelerates a charged particle beam using a high frequency alternating voltage which is applied between two hollow "D"-shaped sheet metal electrodes called "dees" inside a vacuum chamber. The path of the accelerated particle is then bent by a magnetic field into a spiral path (due to the Lorentz force perpendicular to their direction of motion), which tends to cause the particle to be directed back across the gap. By alternately changing the polarity of the electrodes by means of a radio-frequency generating system, the particles are accelerated with each crossing of the gap, thereby increasing the radius of the spiral path of the accelerated particles. When the accelerated particles reach the rim of the chamber a small voltage on a metal plate deflects the beam and hits a target located at the exit point at the rim of the chamber.

For example, U.S. Patent Application Publication No. US 2002/0099405 to Yurek et al., incorporated by reference herein in its entirety, disclose a stent deployment device that includes a flexible elongate catheter having a guidewire lumen to deliver a stent.

Also, for example, U.S. Pat. No. 4,641,104 to Blosser et al, incorporated by reference herein in its entirety, discloses a 60 MeV superconducting medical cyclotron, particularly movable cyclotrons useful for therapeutic purposes. This patent discloses a rotatable superconducting cyclotron with a unique supplementary cooling system for a vessel surrounding superconducting coils which prevents localized boiling of the liquefied gas adjacent the coils. Positively charged deuteron particles or other positively charged atomic particles are accelerated in a helical path between "dees" so as to hit the target tangentially to release neutrons which pass through exit windows and through the collimators as a beam which is directed at the target or patient. The deuterons hitting the target are at between about 25 to 75 MeV, and for medical purposes preferably about 50 MeV. Similarly, U.S. Pat. No. 4,507,616 to Blosser et al., incorporated by reference herein in its entirety, discloses a rotatable superconducting cyclotron that accelerates positively charged particles in a helical path adapted for irradiation of a patient or a target such as beryllium.

Regarding medical use, for example, U.S. Pat. No. 9,056, 199 to Balakin incorporated herein by reference in its entirety, discloses a cyclotron for treating a solid cancer (tumor) of a patient with charged particles using an accelerator configured to deliver the charged particles to the tumor of the patient when the patient is supported by the longitudinal support of the platform, wherein the charged particles are protons. The energy of the charged particles in the altered circulating beam path is preferably in the range of about 30 to 330 MeV/second during irradiation.

Further, U.S. Pat. No. 10,363,439 to Amaldi et al. incorporated herein by reference in its entirety, discloses ion accelerators (cyclotron) for treating Atrial Fibrillation (AF) and arteriovenous malformations (AVMS) by ion beam irradiation. Also, U.S. Patent Application Publication No. 2009/0209805 to Lubock et al., incorporated by reference herein in its entirety, discloses a device with one or more radiation shielding components that partially encircle a radiation source at the treatment location to control emitted radiation from the radiation source to minimize radiation damage to healthy tissue surrounding the body cavity or other site while irradiating tissue not shielded by the radiation shielding components. The device includes an elongated shaft having a longitudinal axis, a distal portion with a treatment location and an arcuate shaped lumen which is offset from the longitudinal axis and which extends within the shaft to the treatment location, an inner lumen extending to the treatment location which is configured to receive a radiation source, and an arcuate shaped radiation shielding component which is slidably disposed within the arcuate shaped lumen and which partially encircles or is configured to partially encircle the treatment location to shield tissue from radiation emitted from the radiation source.

While there are more than 1200 cyclotrons used worldwide to produce radionuclides, there is very little is known about the medical use of cyclotrons for treating neck, head and eye cancer including pediatric cancer, which takes into account the reduced penetration depth that is typically required. Accordingly, there is a need for a compact proton cyclotron for treating medical conditions with radiation therapy, such as pediatric cancer and head, neck and eye tumors, cancers or other medical conditions. Therefore, what is needed are methods and apparatuses using a proton cyclotron for the treatment of medical conditions with radiation therapy, including but not limited to benign and malignant tumors, neurological, lung, head, neck and eye tumors, cancers, abnormalities or conditions, vascular and cardiac conditions and abnormalities, pediatric tumors, cancers and other pediatric abnormalities, cardiac and vascular blockages, and for treating other medical conditions suitable for treatment with radiation therapy, having an energy from 70 MeV to 150 MeV with a beam current in an amount or range suitable for the radiation therapy.

Thus, apparatuses and methods for treating medical conditions with radiation therapy, including but not limited to benign and malignant tumors, neurological, lung, head, neck and eye tumors, cancers, abnormalities or conditions, vascular and cardiac conditions and abnormalities, pediatric tumors, cancers and other pediatric abnormalities, cardiac and vascular blockages, and for treating other medical conditions suitable for treatment with radiation therapy using a proton beam cyclotron therapy addressing the aforementioned needs and problems is desired.

SUMMARY OF INVENTION

Embodiments include apparatuses, systems and methods related to the use of a proton cyclotron for treating cancers and tumors and other medical conditions of a patient, such as desirably for head, neck and eye tumors. The apparatuses, methods and uses include positioning the patient on a support platform, such as in a robotic chair, and irradiating a tumor or cancer using a proton particle beam from the cyclotron for a predetermined time and a predetermined intensity sufficient to treat the tumor or to treat another medical condition, wherein the proton particle beam is generated by the cyclotron having an energy range of from 70 MeV to 150 MeV and having a beam current in an amount suitable for radiation therapy, as can include a variable range of beam current for the radiation therapy, the amount of the beam current being dependent on the use or application for which the radiation therapy is being applied. The apparatuses, methods and uses of the proton cyclotron for treating tumors of a patient, such as head, neck and eye tumors, and pediatric cancers and tumors, or for treating other medical conditions, can further include placing a particle beam splitter to split a portion of the proton particle beam to provide one or more beam lines for treating one or more patients. The apparatuses, systems and methods can further include generating a tomographic image of the patient from an imaging apparatus positioned in close proximity to the patient prior to irradiation of the tumor or cancer or other medical condition.

The apparatuses, systems and methods for using a cyclotron for treating a tumor or cancer or other medical condition of a patient can further include a support platform, such as desirably a robotic chair or table positioned on a floor, the support platform being mounted on a rotatable axis relative to the longitudinal axis (X-axis) of the proton beam as well as rotatable about the vertical axis (Z-axis) of the proton beam. The support platform, such as a robotic chair or patient table, further includes a patient movement constraint system configured to constrain lateral movement of the patient relative to a longitudinal axis of the support platform. The support platform, such as a robotic chair or patient table, is configured to rotate the patient through 180° relative to the X-axis of the particle beam from the cyclotron. Also, the support platform, such as the robotic chair or patient table, is configured to rotate the patient through 90° relative to the Z-axis of the particle beam from the cyclotron. The dedicated use of the cyclotron for treating tumors or cancers, such as pediatric tumors or cancers, or other medical conditions of a patient can further include providing a treatment planning system to generate a treatment plan designed to treat the patient accurately, efficiently and effectively.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION

Figure 1:
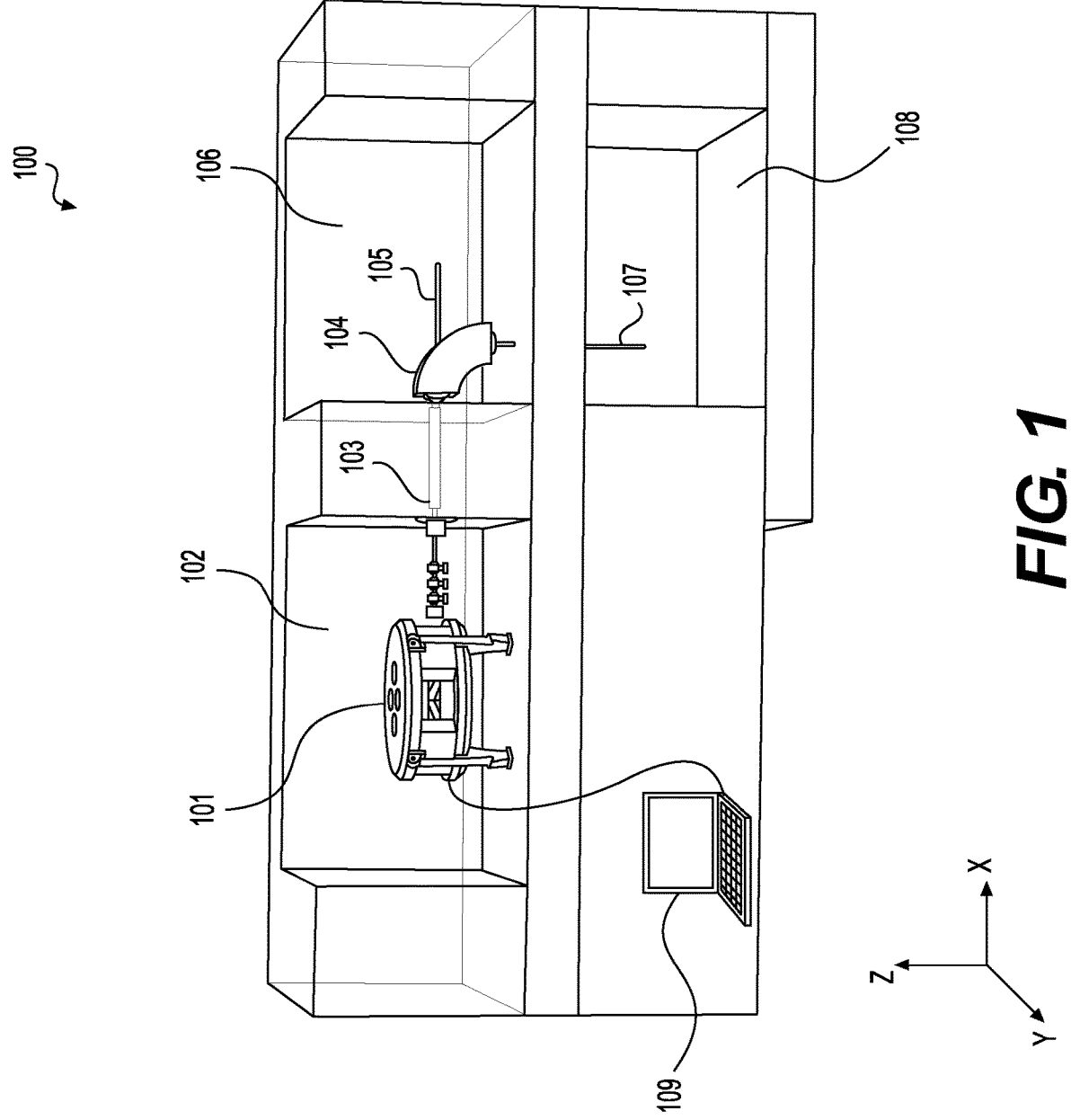
FIG. 1 is a schematic illustrating an overview of an embodiment of a 70 MeV to 150 MeV cyclotron system according to the present invention.

The present disclosure relates to a 70 MeV to 150 MeV cyclotron or proton beam therapy system dedicated for use in treating medical conditions including irradiation of head, neck and eye cancers, including pediatric cancers, and for cardiac, neurological abnormalities, and for treatment of other medical conditions.

The 70 MeV to 150 MeV proton cyclotron delivers the treatment proton beam through a system that constrains the treatment dose by controlling the beam current and energy delivered to individual portions of the tumor or cancer or other medical condition of the patient. Energy constraint allows a simplified beam delivery system. The energy and current intensity allow compact radiation shielding for the accelerator and treatment rooms. One or more patients can be treated simultaneously by splitting the proton beam using a beam splitter placed on the proton beam path. As described herein, embodiments of a comprehensive therapy system for cancer treatment includes an easy to operate proton cyclotron, beam delivery system, multiple nozzles, mobile robotic chair system, imbedded diagnostic device (CT/MR/PET) and a treatment planning system. As to such cyclotrons and cyclotron systems, those disclosed in U.S. Pat. No. 4,641, 104 to Blosser et al., U.S. Pat. No. 4,507,616 to Blosser et al., U.S. Pat. No. 9,056,199 to Balakin and U.S. Pat. No. 10,363,439 to Amaldi et al., all being incorporated by reference herein in their entirety, for example, include features that can be adapted for use in the methods and apparatuses of the various embodiments described herein using the guidance of the instant disclosure.

The apparatuses, systems and methods for using a dedicated cyclotron for treating a tumor or cancer or other medical condition of a patient includes positioning the patient on a support platform, such as desirably in a robotic chair or on a patient table, and irradiating the tumor or other medical condition using a proton particle beam from the cyclotron for a predetermined time sufficient to treat the tumor or cancer or other medical condition, wherein the proton particle beam being produced by the cyclotron has an energy in a range of from 70 MeV to 150 MeV, such as desirably can be obtained by use of a degrader, and a beam current in an amount suitable for radiation therapy, as can include a variable range of beam current for the radiation therapy, the amount of the beam current being dependent on the use or application for which the radiation therapy is being applied. The tumors or cancers or other medical conditions may be localized in the eye, neck and head of the patient or other areas of the patient. The patient can be a pediatric patient or can be an adult patient.

The apparatuses, systems and methods for using a cyclotron for treating tumors and cancers or other medical conditions of a patient can further includes a beam splitter to split a portion of the proton particle beam to provide one or more beam lines for treating multiple patients. The method further includes generating a tomographic image of the patient or target area from an imaging apparatus positioned near the patient prior to irradiating the tumor or cancer or other medical condition. Thus, advantageously, one or more beams can be generated by the cyclotron to treat multiple patients simultaneously, or at about the same time, when the patients are placed in different treatment rooms within the clinic, for example.

The apparatuses, systems and methods for using a cyclotron for treating cancers or tumors, such as tumors of the head, neck and eye, or other medical conditions of a patient can further include generating a tomographic image of the target area to be treated of the patient from an imaging apparatus positioned near the patient prior to irradiating the tumor or cancer or other medical condition. The imaging apparatus and image generated can be a CT or MRI apparatus and image including a tomographic image of the tumor, cancer or medical condition of the patient. In another embodiment, the apparatuses, systems and methods, such as for treating a tumor or cancer of the eye, can include the cyclotron system that includes the use of a suitable camera system, such as a CCD camera or camera system, that tracks the pupil of the eye of the patient, which includes a gating function that is integrated with the cyclotron system that diverts, stops or attenuates the treatment beam from the cyclotron if the eye movement exceeds a predetermined tolerance, for example.

The cyclotron system can include a support platform, such as robotic chair or a patient table, positioned on a floor mounted support in the treatment room; and the support platform can be rotatably mounted for movement on a rotatable axis relative to the longitudinal axis of the proton ion beam generated by the cyclotron. The support platform, such as a robotic chair or a patient table, can further include a patient movement constraint system configured to constrain lateral or vertical movement of the patient, when positioned on or in the support platform. The support platform, such as a robotic chair or a patient table, is configured to rotate the patient through 180° relative to the X-axis of the particle beam delivered from the cyclotron. Further, the support platform, such as a robotic chair or a patient table, is configured to rotate the patient through 90° relative to the Z-axis of the particle beam being delivered from the cyclotron. The dedicated use of cyclotron for treating tumors or cancers or other medical conditions, such as those of the head, neck and eye or pediatric tumors of a patient, can further include providing a treatment planning system to generate a treatment plan designed to treat the patient having such tumors or cancers or other medical condition.

As used herein the term "proton beam therapy" refers to a type of radiation therapy that works by aiming energetic ionizing proton particles accelerated with a particle accelerator, onto a target tumor or target area including a cancer. Proton beam therapy uses protons rather than X-rays to treat cancer. These particles damage the DNA of cells, ultimately causing their death. Cancerous cells, because of their high rate of division and their reduced ability to repair damaged DNA, are particularly vulnerable to attack on their DNA by the proton beams. Proton therapy systems typically include a cyclotron that includes a beam generator and an accelerator, and a beam transport system to move the resulting accelerated protons to a treatment room where the ionizing protons are delivered to a tumor or cancer or other medical condition in a patient's body.

As used herein, the term, "tumor" refers to a mass of tissue that is caused by a growth or accumulation of abnormal cells whether benign or malignant. "Cancer" as used herein refers to any of various types of cancers known to those in the medical field of cancer diagnosis and treatment. Also, as used herein, "medical condition" refers to any of various medical conditions, suitable for treatment with radiation therapy, including but not limited to benign and malignant tumors, neurological, lung, head, neck and eye tumors, cancers, abnormalities or conditions, vascular and cardiac conditions and abnormalities, pediatric tumors, cancers and other pediatric abnormalities, other cancers and tumors, cardiac and vascular blockages, and any other medical condition suitable for treatment with radiation therapy, and should not be construed in a limiting sense.

Referring now to the drawings in greater detail, an exemplary cyclotron system 100, such as a proton cyclotron system 100, such as for the treatment of cancers, tumors, pediatric cancers or other medical conditions, has an energy in a range of from 70 MeV to 150 MeV and has a beam current in an amount suitable for radiation therapy, as can include a variable range of beam current for the radiation therapy, the amount of the beam current being dependent on the use of application for which the radiation therapy is being applied, the proton cyclotron system 100 being diagrammatically illustrated in FIG. 1. As illustrated in FIG. 1, the system 100 includes a compact cyclotron 101 housed in a clinic in a compartment 102 and the system 100 also desirably has or is associated with one or more treatment rooms, such as having at least two treatment compartments 106 and 108. The proton beam 103 is directed to a beam splitter 104 that splits the proton beam 103, into multiple portions, such as one portion 105 and another portion 107 for irradiating the tumors or cancers or other medical conditions of one or more patients residing in different treatment rooms, such as in the treatment compartments 106 and 108, for example. Thus, one or more proton beams can be used to treat one or more patients. A computer controller system 109 is used to control the proton beam and the beam intensity to accurately and precisely deliver protons to a tumor or cancer or other medical condition of a patient. The computer controller system 109, desirably is a single control system for controlling the plurality of the other components of the system 100, such as the proton beam intensity, imaging apparatus and the beam splitter and adapted to include or work in conjunction with a treatment planning system to provide a treatment plan for or during the treatment of the tumor or cancer or other medical condition.

Figure 2:
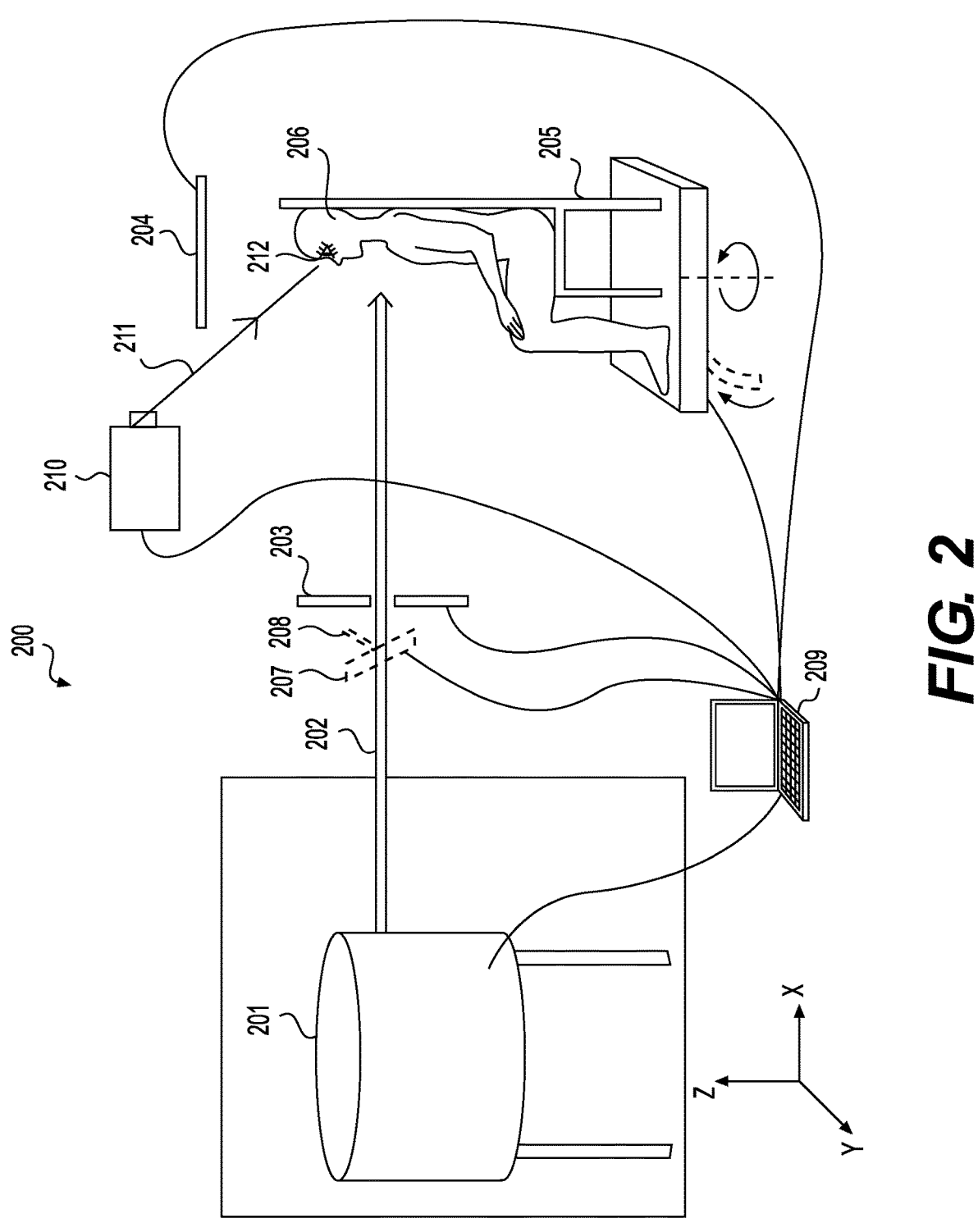
FIG. 2 schematic illustrating an overview of an embodiment of the 70 MeV to 150 MeV cyclotron illustrating the proton irradiation of a patient for tumor or cancer treatment or treatment of other medical conditions according to an embodiment of the present invention.

Referring now to FIG. 2, an illustrative exemplary embodiment of a proton particle beam system 200 as an example of an embodiment of the cyclotron system 100 is provided. The system 200 includes a compact cyclotron 201 housed in a medical clinic facility and the output proton beam 202 is directed to a beam splitter 207 that can split the proton beam 202 in multiple beams, as illustrated by the numeral 208, and the proton beam 202 is optionally placed before a screen 203 to modulate the intensity of the proton beam 202 prior to irradiating the tumor or cancer or other medical condition of a patient 206 that is positioned on a support platform 205, such as a patient table or a robotic chair 205, the support platform 205 being positioned on a floor mounted support, the floor mounted support being illustrated in FIG. 2 by the rectangular block structure on which is positioned the support platform 205. The beam intensity is controlled by a main computer controller 209, or other suitable controller, to accurately and precisely deliver protons, or other radiation, to a tumor or cancer or other medical condition of a patient. For example, the main computer 209 obtains or receives an image, such as a portion of or target area of a body and/or of a tumor or cancer or medical condition to be treated, from an imaging system 204 after interrogating the image of the tumor or cancer or medical condition of the patient. The imaging system 204 can include an imbedded diagnostic device, such as a computed tomography scan imaging system ("CT Scanner"), a magnetic resonance imaging system (MRI Scanner") and a positron emission tomography imaging system ("PET Scanner") or other suitable imaging system, as can depend on the use or application, such as is desirably positioned above the support platform 205, such as the patient table or the robotic chair 205, for example.

In another embodiment, such as for treating the tumors of the eye, the cyclotron system 100, such as the proton particle beam system 200, includes the use of suitable tracking device, such as a CCD camera 210, which tracks, as illustrated by the numeral 211, a pupil 212 of the eye of the patient 206. The CCD camera 210 is controlled by the main computer controller 209, or other suitable controller, in the cyclotron system 100, such as the proton particle beam system 200, and a gating function is integrated in the cyclotron system 100, such as the proton particle beam system 200, that diverts the proton beam 202, or other suitable radiation beam, from the cyclotron system 100, such as the proton particle beam system 200, if the eye movement exceeds a predetermined tolerance, for example.

In a further embodiment, the use of the cyclotron system 100, such as the proton particle beam system 200, can desirably be used for the treatment of various medical conditions, including a cardiac blockage, cardiac or neurological abnormalities, and for treatment of other abnormalities or other medical conditions with radiation, such as is contemplated for patients with coronary artery diseases, for example, such as with the proton beam 202, generated by the cyclotron system 100, such as generated by the proton particle beam system 200. For treating the cardiac blockages or other medical conditions, the cyclotron system 100, such as the proton particle beam system 200, can desirably include the use of a suitable tracking device, such as a CCD camera, or other suitable camera, that monitors or images the cardiac blockages or other medical conditions and assists in targeting the proton beam 200, or other suitable radiation beam, to the specific cardiac blockages to ablate/irradiate the desired tissue from the cardiac artery or to treat other medical conditions. Such method and apparatus could include using known guiding and delivery processes and apparatus adapted for use in the methods and apparatuses for delivering the proton beam, or other suitable radiation beam, using the guidance of the instant disclosure. Embodiments of methods and apparatuses, could include, for example, using a suitable shielded catheter communicating with the proton beam pipe carrying the proton beam generated by the cyclotron system 100, such as the proton particle beam system 200, for delivery to a treatment site of the cardiac blockage or site of another medical condition, as can be coupled with a CCD camera to guide and image the treatment site and the treatment process using the generated the proton beam. Exemplary technology as can be utilized, as modified by the guidance of the instant disclosure, can include, for example, U.S. Pat. No. 10,363,439 to Amaldi et al., incorporated herein by reference in its entirety, which discloses ion accelerators (cyclotron) for treating Atrial Fibrillation (AF) and arteriovenous malformations (AVMS) by ion beam irradiation. Also, such exemplary technology can include U.S. Patent Application Publication No. US 2002/0099405 to Yurek et al., incorporated by reference herein in its entirety, which disclose a stent deployment device that includes a flexible elongate catheter having a guidewire lumen to deliver a stent. Further, such exemplary technology can include U.S. Patent Application Publication No. 2009/0209805 to Lubock et al., incorporated by reference herein in its entirety, which discloses a device with one or more radiation shielding components that partially encircle a radiation source at the treatment location to control emitted radiation from the radiation source to minimize radiation damage to healthy tissue surrounding the body cavity or other site while irradiating tissue not shielded by the radiation shielding components.

Also, as evident from the foregoing, embodiments of the cyclotron system 100, such as the proton particle beam system 200, can be used for the treatment of any of various medical conditions, such as those including cancers, tumors, cardiovascular or neurological abnormalities or other medical conditions, utilizing radiotherapy treatment, as can also include in such medical conditions for treatment other diseases or abnormalities suitable for radiotherapy treatment, and is contemplated for patients with any such medical conditions, and, as such, should not be construed in a limiting sense.

The main computer controller 209, or other suitable controller, in the cyclotron system 100, such as the proton particle beam system 200, also obtains position information and/or timing information from the support platform 205, such as the patient table or the patient robotic chair 205. The main computer controller 209 desirably controls the generation and delivery of the proton beam 202, or other suitable radiation source, within the cyclotron system 100, such as the proton particle beam system 200, such as by controlling the speed, trajectory, energy, intensity and timing of the proton beam 202, or other suitable radiation source beam, that is output from the cyclotron system 100, such as the proton particle beam system 200, for example. The main computer controller 209 also desirably controls the cyclotron system 100, such as the proton particle beam system 200, for targeting of the proton beam 202, or other radiation source, through the beam splitter 207 and for delivery to the patient 206. In an embodiment, for example, one or more components of the support platform 205, such as the patient table or the patient robotic chair 205, are desirably controlled by the main computer controller 209 to position the patient accurately and correctly for the treatment. The support platform 205, such as the patient table or the patient robotic chair 205, is desirably configured to rotate the patient 206 through 180° relative to the longitudinal X-axis of the particle beam, such as the proton beam 202, being delivered and 90° relative to a vertical Z-axis of a treatment room, such as the compartments 106 and 108, for example. The patient 206 is generally immobilized using the restraints on the support platform 205, such as the patient table or the patient robotic chair 205, so that a tightly controlled proton beam 202, or other suitable radiation beam, hits the targeted tumor or cancer or other medical condition in the target area without damaging or limiting damage to healthy tissue. Patient positioning constraints that are used to maintain the patient 206 in a treatment position on the support platform 205, such as the patient table or the patient robotic chair 205, which desirably includes a seat, back support, head support and a foot support. The constraints are applied on these supports on the support platform 205, such as the patient table or the patient robotic chair 205. Here the X-axis, Y-axis, and Z-axis coordinate system is used to describe the orientation of the patient 206 relative to the proton beam 202, or other suitable radiation beam, used for the treatment. The X-axis refers to the moving or movement left or right across the patient 206 and the Z-axis refers to moving or movement up and down of the patient 206 relative to the proton beam 202, or other suitable radiation beam, used for the treatment. The proton beam 202, or other suitable radiation beam, typically is delivered from the cyclotron system 100, such as from the proton particle beam system

200, so as to travel horizontally relative to and in the treatment room, such as the compartments 106 and 108, for example.

In an embodiment, the support platform 205 illustrated in FIG. 2, such as the patient table or the patient robotic chair 205, can be configured to be positioned or converted to the patient table or the robotic chair 205, for example. For example, the support platform 205 illustrated in FIG. 2 converts from the robotic chair 205 into the patient table 205 and can then convert back to the robotic chair 205, as can depend on the use or application. Other suitable irradiation tables can also be substituted for the patient robotic chair 205, for example, as can depend on the use or application, and should not be construed in a limiting sense.

Further, display elements of a display system in the main computer controller 209 are desirably controlled via a main controller in the main computer controller 209. Displays, such as display screens, are typically provided to one or more operators and/or to one or more patients 206. In an embodiment, for example, the main computer controller 209 accurately calculates the delivery of the proton beam 202, or other suitable radiation beam, from all systems of the cyclotron system 100, such as the proton particle beam system 200, for example, such that protons, or other suitable radiation source, are delivered in an optimal therapeutic manner to the patient 206. In embodiments, the cyclotron system 100, such as the proton particle beam system 200, as a proton therapy system, or other suitable radiation source system, can be automated or semi-automated, for example.

The main computer controller 209 controls operations of the cyclotron system 100, such as the proton particle beam system 200, with input from the control panel, such as the keys on the main computer controller 209. It should be understood that the main computer controller 209 may represent, for example, a stand-alone computer, computer terminal, portable computing device, networked computer or computer terminal, or networked portable device. Data, programs or instructions for the treatment and treatment process using the radiation delivery system may be entered into the main computer controller 209 by the user via any suitable type of user interface, such as the control panel or computer keys, and may be stored in a computer readable memory in or associated with the main computer controller 209, which may be any suitable type of computer readable and programmable memory. Calculations and control of the radiation delivery system, such as the cyclotron system 100, such as the proton particle beam system 200, for example, for delivery of the radiation for the treatment from the radiation source are performed by a controller/processor of or associated with the main computer controller 209, which may be any suitable type of computer processor, and may be displayed to the user on a display of or associated with the main computer controller 209, which may be any suitable type of computer display, such as a liquid crystal display (LCD) or a light emitting diode (LED) display, for example. Though not shown, another display can be connected to main computer controller 209 to provide or show desired information related to the treatment, treatment process, and the like, for example.

The controller/processor in or associated with the main computer controller 209 may be associated with, or incorporated into, any suitable type of computing device, for example, a personal computer or a programmable logic controller (PLC) or an application specific integrated circuit (ASIC). The display of the main computer controller 209, the controller/processor of or associated with the main computer controller 209, the memory in or associated with the main computer controller 209, and any associated computer readable media are in communication with one another by any suitable type of data bus or by wireless communication, as is well known in the art. In this manner, the main computer controller 209 is in communication with the cyclotron system 100, such as the proton particle beam system 200, for delivery and control of the treatment, for example.

Examples of computer readable media in or associated with the main computer controller 209 include a magnetic recording apparatus, non-transitory computer readable storage memory, an optical disk, a magneto-optical disk, and/or a semiconductor memory (for example, RAM, ROM, etc.). Examples of magnetic recording apparatus that may be used in addition to the memory in or associated with the main computer controller 209, or in place of such memory, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Figure 3:
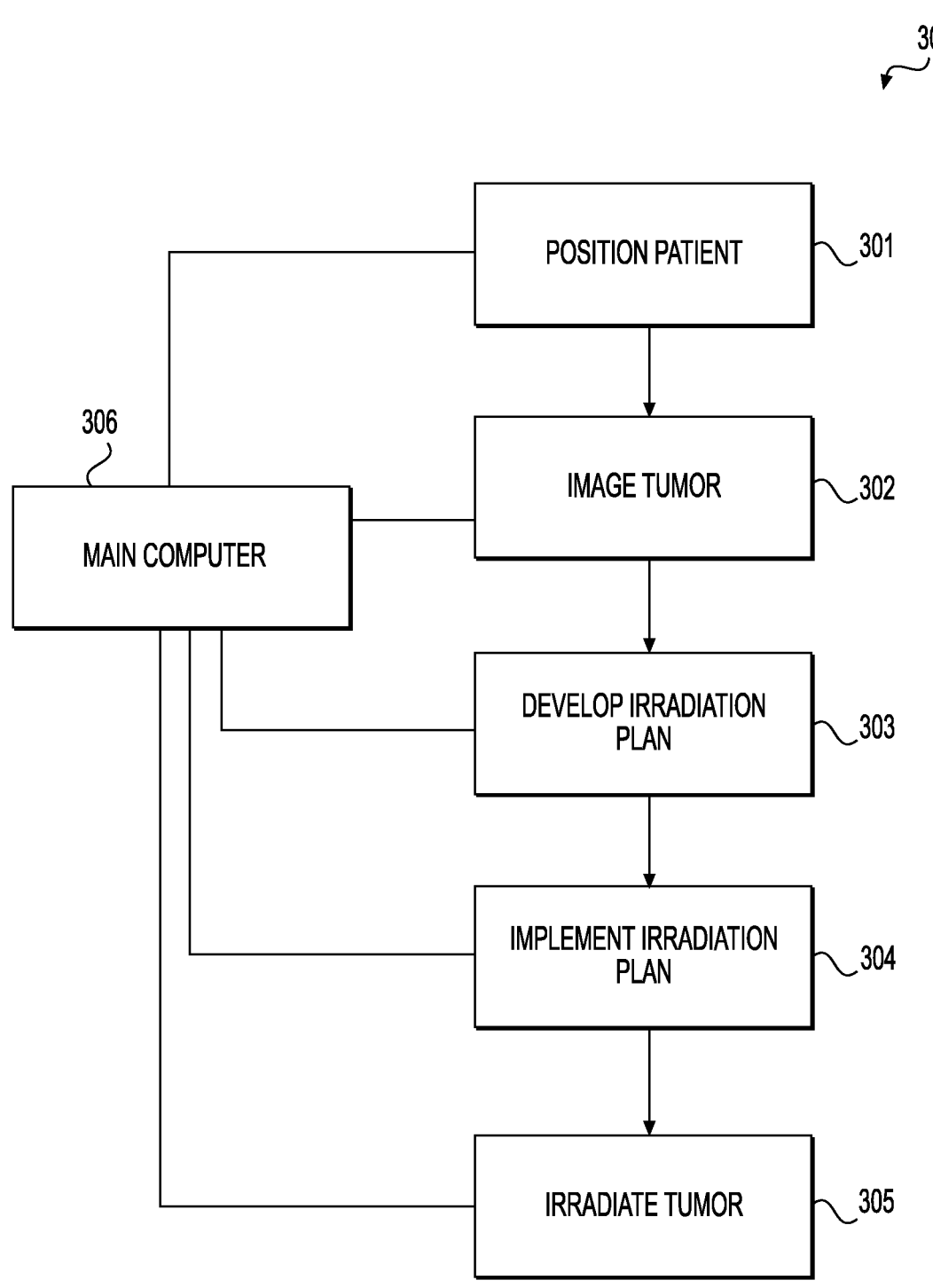
FIG. 3 is a block diagram illustrating an embodiment of a method for proton beam therapy using the proton beam from a 70 MeV to 150 MeV cyclotron according to an embodiment of the present invention.

Referring now to with reference to FIG. 3, an embodiment of a method for tumor/cancer therapy or for treatment of other medical conditions is provided using the cyclotron system 100, such as the proton particle beam system 200, for example. The patient 206 is first positioned at step 301 in or on the support platform 205, such as the patient table or the patient robotic chair 205, and then the tumor/cancer or other medical condition of the patient is imaged at step 302 by the imaging device 204 that is desirably positioned near the patient 206. Subsequently a treatment plan, such as a proton particle irradiation plan, is developed at step 303, such as by a treatment planning system in or associated with the main computer controller 209. Then, the proton particle irradiation plan, or other suitable radiation plan, is implemented for delivery of the radiation treatment to the patient 206, such as with the proton beam 202, at step 304. Then, at step 305, the cyclotron system 100, such as the proton particle beam system 200, under control of the main computer controller 209, generates the proton beam 202 to irradiate the tumor or cancer or other medical condition with a predetermined proton beam intensity, such as of a sufficient radiation intensity, or other suitable radiation intensity, and of a sufficient predetermined duration at step 305. Further additional optional steps can be integrated into embodiments of the methods, apparatuses and systems for the radiation treatment. For example, the positioning, imaging, and irradiation steps are optionally integrated with patient translation control or patient rotation control using the main computer controller 209 at step 306. Additionally, any of the steps described herein are optionally coordinated and integrated with the proton particle beam generation, intensity and/or delivery. Also, any of the steps are optionally coordinated with X-axis, Y-axis beam trajectory control, delivered energy control, delivered intensity control, timing of charged particle delivery, and/or distribution of radiation to limit or substantially avoid striking or irradiating healthy tissue, for example.

It is to be understood that the embodiments of the methods, apparatus and systems taught and described herein in terms of a proton beam are not intended to be limited to that of a proton beam and are illustrative of and are applicable to of any of various suitable charged particle beam systems, as can depend on the use or application, and should not be construed in a limiting sense. Also, in addition to treating human medical conditions, the embodiments of the methods, apparatuses and systems taught and described herein are also applicable to veterinary medicine for treatment of various medical conditions in animals that are suitable for treatment with radiation therapy.

It is to be understood that the present invention is not limited to the embodiments described above but encompasses any and all embodiments within the scope of the following claims.

We claim:

1. A method of using a cyclotron for treating a tumor, a cancer or a medical condition of a plurality of patients residing in different treatment rooms, comprising the steps of:

positioning each patient of the plurality of patients residing in different treatment rooms on a respective support platform;

placing a particle beam splitter to split a proton particle beam from the cyclotron into multiple beams to provide a plurality of proton particle beams for treating the plurality of patients residing in different treatment rooms; and providing an irradiation dose to the tumor, the cancer or the medical condition of the plurality of patients using for each patient of the plurality of patients a proton particle beam of the plurality of proton particle beams from the particle beam splitter for a predetermined time to treat the tumor, the cancer or the medical condition, wherein the proton particle beam produced by the cyclotron has an energy in a range of from 70 MeV to 150 MeV.

2. The method according to claim 1, further comprising the step of: generating a tomographic image of the tumor, the cancer or the medical condition from an imaging apparatus positioned near the patient prior to irradiating the tumor, the cancer or the medical condition.

3. The method according to claim 1, further comprising the step of: adjusting the irradiation dose by controlling a power and a beam intensity output of the cyclotron.

4. The method according to claim 1, wherein the tumor, the cancer or the medical condition is localized in the eye, neck or head of the patient.

5. The method according to claim 1, wherein the support platform is positioned on a floor mounted support that is rotatable relative to a longitudinal axis (X-axis) of a delivered one of said plurality of proton particle beams from the particle beam splitter.

6. The method according to claim 1, wherein the support platform is positioned on a floor mounted support that is rotatable or moveable up and down relative to a vertical axis (Z-axis) of a delivered one of said plurality of proton particle beams from the particle beam splitter.

7. The method according to claim 1, wherein the support platform comprises a patient movement constraint system configured to constrain lateral movement of the patient.

8. The method according to claim 1, wherein the support platform comprises a robotic chair configured to rotate or move the patient through 180° relative to a longitudinal axis (X-axis) and through 90° relative to a vertical axis (Z-axis) of a delivered one of said plurality of proton particle beams from the particle beam splitter.

9. The method according to claim 1, wherein the support platform is a robotic chair.

10. The method according to claim 1, wherein the support platform converts from a robotic chair to a patient table.

11. A method of using a cyclotron for treating a cardiac blockage of a plurality of patients residing in different treatment rooms, comprising the steps of:

positioning each patient of the plurality of patients residing in different treatment rooms on a respective support platform;

placing a particle beam splitter to split a proton particle beam from the cyclotron into multiple beams to provide a plurality of proton particle beams for treating the plurality of patients residing in different treatment rooms; and providing an irradiation dose to the cardiac blockage of each patient of the plurality of patients using for each patient of the plurality of patients a proton particle beam of the plurality of proton particle beams from the particle beam splitter for a predetermined time to treat the cardiac blockage, wherein the proton particle beam produced by the cyclotron has an energy in a range of from 70 MeV to 150 MeV.

12. An apparatus for treatment of a cardiac blockage of a plurality of patients residing in different treatment rooms, comprising:

a cyclotron configured to provide a proton particle beam;

a particle beam splitter to split the proton particle beam from the cyclotron into multiple beams to provide a plurality of proton particle beams to provide an irradiation dose for treating the cardiac blockage of each patient of the plurality of patients residing in different treatment rooms, wherein the proton particle beam produced by the cyclotron has an energy in a range of from 70 MeV to 150 MeV; and a computer controller configured to control the cyclotron to generate and deliver the proton particle beam and to control delivery of the plurality of proton particle beams from the particle beam splitter for the treatment of the cardiac blockage of each patient of the plurality of patients.

13. An apparatus for treatment of a tumor, a cancer or a medical condition of a plurality of patients residing in different treatment rooms, comprising:

a cyclotron configured to provide a proton particle beam;

a particle beam splitter to split the proton particle beam from the cyclotron into multiple beams to provide a plurality of proton particle beams to provide an irradiation dose for treating the tumor, the cancer or the medical condition of each patient of the plurality of patients residing in different treatment rooms, wherein the proton particle beam produced by the cyclotron has an energy in a range of from 70 MeV to 150 MeV; and a computer controller configured to control the cyclotron to generate and deliver the proton particle beam and to control delivery of the plurality of proton particle beams from the particle beam splitter for the treatment of the tumor, the cancer or the medical condition of each patient of the plurality of patients.

14. The apparatus according to claim 13, further comprising:

a support platform configured for respectively receiving a patient of the plurality of patients, the support platform being configured to selectively convert from a robotic chair to a patient table and back to the robotic chair.

15. The apparatus according to claim 13, further comprising:

a support platform configured for respectively receiving a patient of the plurality of patients, the support platform configured to be positioned on a floor mounted support that is rotatable or moveable relative to a vertical axis (Z-axis) of a delivered one of said plurality of proton particle beams from the particle beam splitter.

16. The apparatus according to claim 15, wherein the support platform comprises a robotic chair configured to rotate or move the patient through 180° relative to a longitudinal axis (X-axis) and through 90° relative to the vertical axis (Z-axis) of the delivered one of said plurality of proton particle beams from the particle beam splitter.

\*   \*   \*   \*   \*